Figure 1:
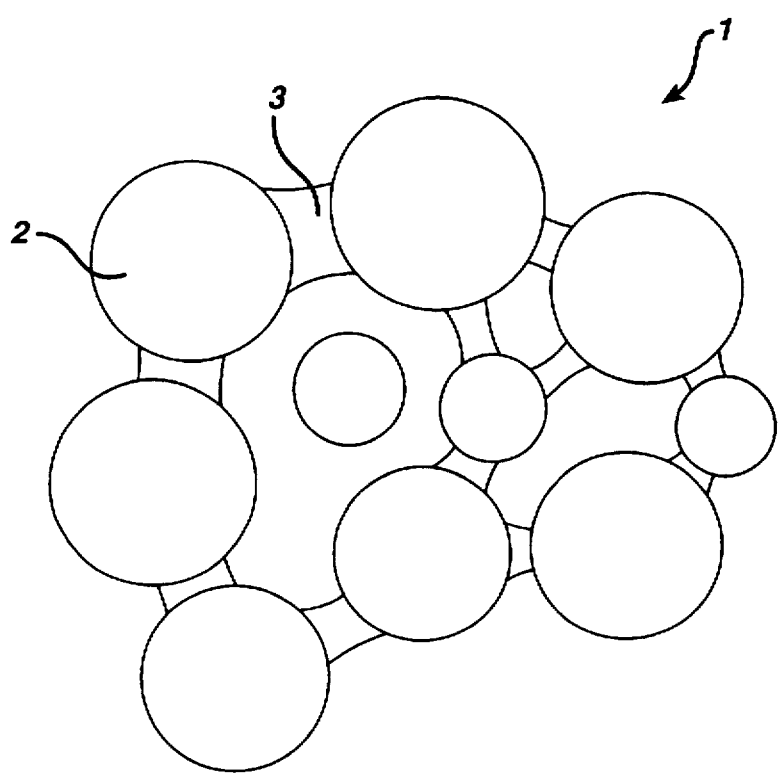

United States Patent [19]
Arnold

[11] Patent Number: 5,766,631
[45] Date of Patent: Jun. 16, 1998

[54] WOUND IMPLANT MATERIALS

[76] Inventor: Peter Stuart Arnold, 82 Raikes Road, Skipton, North Yorkshire BD23 1LS, United Kingdom

[21] Appl. No.: 461,791

[22] Filed: Jun. 5, 1995

Related U.S. Application Data

[62] Division of Ser. No. 309,828, Sep. 21, 1994.

[30] Foreign Application Priority Data

Sep. 21, 1993 [GB] United Kingdom ............ 9319447

[51] Int. Cl.$^6$ ............ A61K 47/30; A61K 27/00
[52] U.S. Cl. ............ 424/486; 424/489; 424/423; 424/426
[58] Field of Search ............ 424/486

[56] References Cited

U.S. PATENT DOCUMENTS

| | | |
|---|---|---|
| 4,837,285 | 6/1989 | Berg et al. . |
| 4,849,141 | 7/1989 | Fujioka et al. ............ 424/426 |
| 4,970,298 | 11/1990 | Silver et al. . |
| 5,354,556 | 10/1994 | Sparks et al. . |
| 5,356,629 | 10/1994 | Sander et al. ............ 424/423 |
| 5,456,917 | 10/1995 | Wise et al. ............ 424/426 |

FOREIGN PATENT DOCUMENTS

| | | |
|---|---|---|
| 0274898 | 7/1988 | European Pat. Off. . |
| 0381543 | 8/1990 | European Pat. Off. . |
| 522 569 | 1/1993 | European Pat. Off. . |
| 0562864 | 9/1993 | European Pat. Off. . |
| 03023864 | 1/1991 | Japan . |
| 2 215 209 | 9/1989 | United Kingdom . |
| 89/07935 | 9/1989 | WIPO . |
| 90/00060 | 1/1990 | WIPO . |
| 91/06286 | 5/1991 | WIPO . |

OTHER PUBLICATIONS

British Patent Office Search Report for GB 9319447.0.
European Patent Office Search Report for EP 94 30 6874.
Database WPI, Week 9111, Derwent Publications Ltd., London, GB; AN 91–077288 (Gunter & Zimmermann) (31 Jan. 1991).

*Primary Examiner*—Peter F. Kulkosky

[57] ABSTRACT

Wound implant materials are described comprising a plurality of bioabsorbable microspheres bound together by a bioabsorbable matrix, such as in a freeze-dried collagen matrix. The microspheres preferably comprise over 30% of the volume of the material, and preferably have diameters of 10 μm to 1500 μm. The microspheres and/or the matrix preferably comprise a polylactic/polyglycolic copolymer, collagen, cross-linked collagen, hyaluronic acid, cross-linked hyaluronic acid, an alginate or a cellulose derivative. The resulting implants are stronger and more slowly resorbed than conventional collagen sponge implants. Better control over the porosity of the implant is achieved.

21 Claims, 1 Drawing Sheet

WOUND IMPLANT MATERIALS

This is a division of application Ser. No. 08/39,828, filed Sep. 21, 1994, which is hereby incorporated by reference.

The present invention relates to novel bioabsorbable materials for use as or in wound implants, and to methods of preparation of those materials.

Healing of cavity wounds depends on the production by the wound of substantial quantities of matrix materials and granulation tissue as natural filler, and the dekeratinization and migration of cells at the periphery of the wound across the moist surface of the neoangiogenic matrix. Currently, such wounds are treated with dressings designed to maintain a moist environment and to prevent fluid loss, infection, adherence and trauma. Additionally, alginates and hydrocolloids have been used to absorb excess exudate and contribute to granulation induction. These materials have the obvious disadvantage that they are not designed to be 'absorbed' by the wound and therefore must be removed from the cavity, usually with irrigation and disruption of wound reparation.

An effective alternative to alginates and hydrocolloids would be similar materials constructed from absorbable biomaterials with a determined pharmacological fate that could be left in situ throughout and after wound healing. Hitherto, the materials suggested for this purpose have included bioabsorbable sponges formed by freeze-drying solutions or suspensions of bioabsorbable polymers.

Advantageously, these bioabsorbable polymers are natural biopolymers such as collagen, fibrin, fibronectin or hyaluronic acid. Such materials are not only highly biocompatible and biodegradable, but they can also assist wound healing by promoting the proliferation of fibroblasts, and by promoting angiogenesis.

For example, U.S. Pat. No. 4,970,298 (Frederick H. Silver et al) describes a biodegradable collagen matrix suitable for use as a wound implant. The matrix is formed by freeze drying a dispersion containing collagen, crosslinking the collagen via two crosslinking steps and freeze-drying the crosslinked matrix. The matrix may also contain hyaluronic acid and fibronectin.

WO90/00060 (Collagen Gorporation) describes collagen implants that are formed by flash freezing and then freeze-drying a suspension of collagen fibrils without chemical cross-linking. The implants have a bulk density of 0.01 to 0.3 g/cm$^3$ and a pore population in which at least about 80% of the pores have an average pore size of 35 to 250 µm. This wound healing matrix also serves as an effective sustained delivery system for bioactive agents.

EP-A-0274898 (Ethicon Inc.) describes an absorbable implant material having an open cell, foam-like structure and formed from resorbable polyesters, such as poly-p-dioxanone, other polyhydroxycarboxylic acids, polylactides or polyglycolides. The open-cell plastic matrix is reinforced with one or more reinforcing elements of a textile nature formed from a resorbable plastic and embedded in the matrix. The open-cell plastic matrix is made by freeze-drying a solution or suspension of the plastic material in a non-aqueous solvent. The pore size of the open-cell plastic matrix is from 10 to 200 µm.

JP-A-03023864 (Gunze KK) describes a wound implant material comprising a collagen sponge matrix reinforced with fibres of poly-L-lactic acid. The collagen sponge matrix is formed by freeze drying a solution of porcine atherocollagen.

The above bioabsorbable sponge implants are formed by freeze-drying solutions or suspensions of a bioabsorbable material in a solvent. However, it is generally difficult to control the pore size and overall density of sponge materials made in this way. Normal freeze-drying procedures result in sponges having large pores and low density. Such sponges are weak, and tend to be resorbed too quickly to be suitable in practice for use as wound implants. The physical weakness of the sponges has been addressed by embedding bioabsorbable reinforcing fibres in the sponge matrix, but the reinforcing fibres cannot prevent the rapid reakdown and resorption of the sponge matrix in situ.

The rate of resorption of the freeze-dried sponges has ypically been reduced by chemical cross-linking of the polymer making up the sponge: For example, the collagen in a collagen sponge can be cross-linked with carbodiimide or glutaraldehyde to make it insoluble and to reduce the rate of breakdown of the collagen by collagenase present at the wound site. This chemical cross-linking by its very nature makes the collagen less biocompatible and less wound-friendly. Moreover, even with cross-linking, it is difficult to obtain a controlled and optimised rate of cellular invasion and resorption of the implant.

Some control over the pore size and density of freeze-dried sponges can be achieved by varying parameters such as the concentration of the starting solution or suspension and the rate of freezing. Smaller pore sizes can be obtained by "flash-freezing" the solution or suspension, since this results in the formation of smaller ice crystals in the frozen solution. However, even flash-freezing followed by freeze drying results in a sponge of quite low bulk density, with highly disperse pore sizes typically in the range of 35 to 250 µm.

Accordingly, it is an object of the present invention to provide a bioabsorbable wound implant material that has high strength and controlled porosity.

The present invention provides a wound implant material comprising a plurality of bioabsorbable microspheres bound together by a bioabsorbable matrix. The term "bioabsorbable microspheres" refers to substantially spherical particles of one or more bioabsorbable materials. Preferably, the degree of non-sphericality of the particles, as defined by the average ratio of the largest diameter to the smallest diameter of each particle, is less than 2.0, more preferably less than 1.5 and most preferably less than 1.2. A ratio of 1.0 would correspond to perfectly spherical particles. The microspheres may be solid or hollow, or may comprise microcapsules encapsulating a solid, liquid or gel comprising a pharmacologically active substance, a biopolymer or a growth factor. The microspheres need not be of uniform size, but preferably at least 90% of the microspheres have diameters between 50 µm and 1500 µm. More preferably, at least 90% of the microspheres have diameters between 200 µm and 1000 µm. Most preferably, at least 90% of the microspheres have diameters between 500µm and 800 µm.

The bioabsorbable matrix may be a solid or a semi-solid such as an aqueous gel of a biopolymer. Preferably, the matrix is a bioabsorbable solid obtained by air drying or freeze-drying a gel solution or suspension of a bioabsorbable polymer in a solvent. The bioabsorbable matrix may comprise the same material as the microspheres, or may comprise other materials.

It can thus be seen that the wound implant materials according to the present invention are aggregates of solid microspheres bound together by the bioabsorbable matrix material. Preferably, the materials contain at least 30% by volume of the microspheres. More preferably, the materials contain at least 40% by volume, and most preferably at least 50% by volume of the microspheres. It will be appreciated that, based on closest packing of spheres, the materials may contain up to 72% by volume of microspheres of identical size, and a still higher fraction by volume if the microspheres are size disperse.

The porosity of the materials according to the present invention may be controlled both by varying the size of the microspheres and by varying the volume fraction of the microspheres in the material. Average pore sizes in the range 50 µm–250 µm have been described as optimal for tissue ingrowth.

The preferred material for the bioabsorbable matrix is collagen in solid, gel or sponge form. The volume of the bioabsorbable matrix is not more than 70% of the total volume of the material according to the present invention. Preferably, the bioabsorbable matrix does not occupy the whole of the interstitial space between the microspheres, but instead is concentrated in the region of contact between microspheres, where it functions as a glue to hold the microspheres together. Preferably, the bioabsorbable matrix materials do not comprise more than 20% by volume and/or 20% by weight of the materials according to the present invention, and more preferably they do not comprise more than 10% by volume and/or 10% by weight of the materials.

Preferably, the microspheres and/or the matrix comprise one or more bioabsorbable polymers independently selected from the group consisting of polymers or copolymers of lactic acid and/or glycolic acid, collagen, cross-linked collagen, hyaluronic acid, cross-linked hyaluronic acid, an alginate or a cellulose derivative. Preferably, the microspheres or the matrix, or both, additionally contain pharmaceutically active compounds such as fibronectin, a cytokine, a growth factor, an antiseptic, an antibiotic, a steroid or an analgesic.

The wound implant materials according to the present invention may be reinforced by including fibres or a mesh of a suitable bioabsorbable polymer such as polylactic/polyglycolic acid or oxidised regenerated cellulose.

It will also be appreciated that single pieces of the materials according to the present invention can be made with more than one porosity. For example, a layered structure could be made by building up layers containing microspheres of different sizes, thereby giving different porosities in different layers of the material.

The wound implant materials according to the present invention can be cut into any suitable shape for use as or in a wound implant.

The present invention also encompasses a method of making a wound implant material as described above, comprising the steps of: preparing bioabsorbable microspheres; dispersing the bioabsorbable microspheres in a solution or suspension of a bioabsorbable material in a solvent; and removing the solvent by evaporation. Preferably, the solvent is removed by freeze drying.

The microspheres may be made by any of the methods known in the art. These methods are reviewed, for example, by R. C. Oppenheim in *Polymeric Particles and Microspheres*, Guiot and Couvreur, editors, Chapter I, pp 1–25 (CRC Press, 1986). The most commonly used method comprises dispersing a water-insoluble bioabsorbable polymer in a nonaqueous, volatile solvent, followed by mixing the solvent with water and an emulsifier, emulsifying the mixture and then evaporating the solvent under reduced pressure. Crosslinking agents and/or pharmaceutically active compounds may be included in the emulsion. Methods of making bioabsorbable microspheres are also described in U.S. Pat. No. 3,092,553, EP-A-0119076, EP-A-0351296, WO91/06286 and WO91/15193. The as-prepared microspheres are generally size disperse, having diameters in the range 0.01 µm to 1500 µm. It is generally found that larger microspheres suitable for the practice of the present invention are obtained from water-in-oil emulsion by crosslinking and evaporation. Smaller microspheres are obtained from oil-in-water emulsions.

Large biopolymer microspheres suitable for the practice of the present invention may also be obtained by the extrusion of a laminar flow of an aqueous dispersion of the biopolymer. The laminar flow is then broken up by vibrations into droplets, which fall into a cross-linking bath to form the cross-linked microspheres.

Specific techniques for forming biopolymer microspheres in the size range of interest for the present invention are described in detail in EP-A-0381543 and WO92/02254. Biopolymer microspheres suitable for the practice of the present invention may be obtained from Bioetica, 32 Rue Saint-Jean-de-Dieu, 69007 Lyon, France, under the Trade Mark "Type A Collaspheres".

Preferred size ranges can be isolated by filtration or centrifugation.

An embodiment of the present invention will now be described further, by way of example, with reference to the accompanying drawing, which shows a schematic cross-section through a material according to the present invention.

EXAMPLE 1

A cross-linked ester of hyaluronic acid prepared as described in EP-A-0265116 (Fidia SpA) is dissolved in a volatile organic solvent and fibrous collagen is added to the resulting solution. The solution is emulsified in water using gelatin as the emulsifier. The organic solvent is removed under reduced pressure at room temperature to leave a suspension of hyaluronic acid ester/collagen microspheres dispersed in the water. Microspheres in the size range 600 µm–800 µm are isolated by filtration, dried, and mixed into a 7% collagen/water gel. The mixture is then freeze-dried and cut into 5 cm×5 cm×0.5 cm doses. The density of the material is 50 mg/cm$^3$, of which 3 mg/cm$^3$ is the collagen matrix and 47 mg/cm$^3$ is the microspheres.

The reticulation of the resulting implant material is assessed by electron microscopy. This shows consistent pore sizes of between 50 and 250 µm.

A cross-section through resulting implant material is shown schematically in FIG. 1. Referring to the Figure, the implant material 1 comprises microspheres 2 stuck together by the collagen matrix 3. The matrix 3 does not fill the whole of the interstitial space between the microspheres, but leaves the pores between the microspheres substantially open.

EXAMPLE 2

A wound implant material is prepared as in Example 1, with addition of hyaluronic acid at a concentration of 0.1 to 2 mg/cm$^3$ based on the weight of the dry finished material, to the collagen/water gel. The resulting material benefits from the chemotactic effect of hyaluronic acid assisting cellular ingrowth.

The materials prepared as above have a more consistent pore size than conventional bioabsorbable sponge implants. This allows more precise control of cellular ingrowth and rate of resorption in situ. The bulk density of the materials according to the present invention (10–100 mg/cm$^3$) may be made higher than that of conventional freeze-dried sponges depending on the application, resulting in a stronger and more slowly absorbed implant. Furthermore, the rate of absorption of the microspheres can be tailored within a wide range. This allows, for example, the preparation of implants that-are absorbed more slowly than a conventional freeze-dried collagen sponge.

The above examples are intended for the purpose of illustration only. Many other embodiments falling within the scope of the accompanying claims will be apparent to the skilled reader.

I claim:

1. A reticulated wound implant material comprising a plurality of bioabsorable microspheres bound together by a bioabsorable matrix which extends between adjacent microspheres, the wound implant having open pores formed by and between adjacent microspheres and the matrix material, the approximate size and volume fraction of the microspheres in the implant material being preselected to provide an approximate size of the pores of between 50 mm and 250 mm whereby to enhance tissue ingrowth into the wound implant material, and wherein at least one of the microspheres and the matrix contains a medicament selected from the group consisting of: fibronectin, a cytokine, a growth factor, an antiseptic, an antibiotic, steroid and an analgesic; and wherein the microspheres are formed of a first bioadsorable biopolymer and the matrix is formed of a second bioabsorable bipolymer, wherein the first bioabsorable biopolymer and the second bioabsorable biopolymer are the same or different and wherein each of the first and second bioabsorable biopolymers are selected from the group consisting of: a polymer or copolymer of lactic acid and/or glycolic acid, collagen, cross-linked collagen, hyaluronic acid, cross-linked hyaluronic acid, an alaginate and a cellulose derivative.

2. A wound implant material according to claim 1 wherein the microspheres comprise at least 30 percent of the volume of the material.

3. A wound implant material according to claim 1 wherein the microspheres comprise at least 40 percent of the volume of the material.

4. A wound implant material according to claim 1 wherein the microspheres comprise at least 50% of the volume of the material.

5. A wound implant material according to claim 1 wherein the matrix, is a solid material.

6. A wound implant material according to claim 5, wherein the matrix material is freeze-dried.

7. A wound implant material according to claim 1 wherein the microspheres comprise hollow microspheres or hollow capsules.

8. A wound implant material according to claim 1 wherein the microspheres are formed of a first bioabsorbable biopolymer and the matrix is formed of a second bioabsorbable biopolymer, wherein the first bioabsorbable biopolymer and the second bioabsorbable biopolymer are the same or different and wherein each of the first and second bioabsorbable biopolymers are selected from the group consisting of: |comprise| a polymer or copolymer of lactic acid and/or glycolic acid, collagen, cross-linked collagen, hyaluronic acid, cross-linked hyaluronic acid, an alginate and a cellulose derivative.

9. A wound implant material according to claim 1 wherein at least 90% of the microspheres have diameters between 50 μm and 1500 μm.

10. A wound implant material according to claim 9 wherein at least 90% of the microspheres have diameters between 200 μm and 1000 μm.

11. A wound implant material according to claim 10, wherein at least 90% of the microspheres have diameters between 500 μm and 800 μm.

12. A process of preparing a reticulated wound implant material, comprising the steps of:

preparing bioabsorbable microspheres;

dispersing the bioabsorbable microspheres in a solution or suspension of a bioabsqrbable material in a solvent; and removing the solvent by evaporation;

forming pores by and between the microspheres and matrix, and adjusting the size of the microspheres and their density within the matrix to achieve an average pore size of between 50 mm and 250 mm;

wherein the microspheres and/or the bioabsorbable material contain a medicament selected from the group consisting of: fibronectin, a cytokine, a growth factor, an antiseptic, an antibiotic, a steroid and an analgesic; and wherein the microspheres are formed of a first bioabsorbable biopolymer and the matrix is formed of a second bioabsorbable biopolymer, wherein the first bioabsorbable biopolymer and the second bioabsorbable biopolymer are the same or different and wherein each of the first and second bioabsorbable biopolymers are selected from the group consisting of: a polymer or copolymer of lactic acid and/or glycolic acid, collagen, cross-linked collagen, hyaluronic acid, cross-linked hyaluronic acid, an alginate and a cellulose derivative.

13. A process according to claim 12, wherein the solvent is removed by freeze-drying.

14. A wound implant material according to claim 1 wherein the medicament comprises fibronectin.

15. A wound implant material according to claim 1 wherein the medicament comprises a cytokine.

16. A wound implant material according to claim 1 wherein the medicament comprises a growth factor.

17. A wound implant material according to claim 1 wherein the medicament comprises an antiseptic.

18. A wound implant material according to claim 1 wherein the medicament comprises a steroid.

19. A wound implant material according to claim 1 wherein the medicament comprises an antibiotic.

20. A wound implant material according to claim 1 wherein the medicament comprises an analgesic drug.

21. A wound implant material according to claim 2 wherein the first and second bioabsorbable biopolymers each comprise collagen.

* * * * *